United States Patent [19]

Reddy

[11] Patent Number: 4,834,113

[45] Date of Patent: May 30, 1989

[54] PROPHYLACTIC DEVICE

[76] Inventor: A. V. K. Reddy, 1042 Jade Dr., Hanna, Wyo. 82327

[21] Appl. No.: 205,933

[22] Filed: Jun. 13, 1988

Related U.S. Application Data

[63] Continuation-in-part of Ser. No. 84,622, Aug. 11, 1987, abandoned, which is a continuation-in-part of Ser. No. 7,104, Jan. 27, 1987, abandoned.

[51] Int. Cl.⁴ .............................................. A61F 5/44
[52] U.S. Cl. .................................... 128/830; 128/844; 604/330; 604/353
[58] Field of Search ........ 128/830, 832, 835, 842–844, 128/850, 856, 883, 884; 604/329–331, 346–354

[56] References Cited

U.S. PATENT DOCUMENTS

| | | | |
|---|---|---|---|
| D. 254,808 | 4/1980 | Meldahl . | |
| D. 288,485 | 2/1987 | Denno .................. | D24/51 |
| 899,251 | 9/1908 | Graham . | |
| 2,123,343 | 7/1938 | Rightsell .............. | 128/844 |
| 2,406,600 | 8/1946 | Forestiere ........... | 128/844 |
| 2,534,934 | 12/1950 | Viniegra . | |
| 2,591,783 | 4/1952 | Craddock ............ | 128/842 |
| 2,873,740 | 2/1959 | Wainwright . | |
| 3,452,749 | 7/1969 | Riedell . | |
| 3,536,066 | 10/1970 | Ludwig . | |
| 3,749,096 | 7/1973 | Donaldson . | |
| 3,759,254 | 9/1973 | Clark . | |
| 4,004,591 | 1/1977 | Friemark . | |
| 4,368,733 | 1/1983 | Sanidas . | |
| 4,589,875 | 5/1986 | Stringer . | |
| 4,630,602 | 12/1986 | Strickman et al. . | |
| 4,664,104 | 5/1987 | Jaicks .................. | 128/830 |
| 4,735,621 | 4/1988 | Hessel . | |
| 4,738,357 | 4/1988 | Martin et al. . | |

FOREIGN PATENT DOCUMENTS

| | | | |
|---|---|---|---|
| 1158507 | 12/1983 | Canada ................................ | 604/349 |
| 0027731 | 4/1981 | European Pat. Off. . | |
| 0135283 | 3/1985 | European Pat. Off. . | |
| 0210413 | 9/1909 | Fed. Rep. of Germany ...... | 128/830 |
| 0117234 | 10/1926 | Switzerland ........................ | 604/349 |

OTHER PUBLICATIONS

"Outline for Successful Prophylactic Program", The Heminway Press, 1934 The Gee Bee Company, pp. 7–16.

"In vitro and In vivo Evaluation of Latex Condoms Using a Two-Phase Nonoxynol 9 System" Fertility and Sterility, vol. 43, Jun. 1985 pp. 931–936 Rodgers-Neame et al.

Primary Examiner—C. Fred Rosenbaum
Assistant Examiner—Mario Costantino
Attorney, Agent, or Firm—John C. Evans

[57] ABSTRACT

A prophylactic device is described which is adapted to be worn by a person to prevent the transmission of disease and sperm during sexual intercourse. The device may be adapted for use by a female person or by a male person. The device includes an elongated hollow pouch which has an open end and a closed end. The pouch has a thin wall member which is flexible and elastic. A continuous flange member is attached to the open end of the pouch and extends outwardly around the opening in the pouch. Attachment means secured to the flange attaches the device to the person wearing it. The device may be in the form of a garment worn by the person.

1 Claim, 13 Drawing Sheets

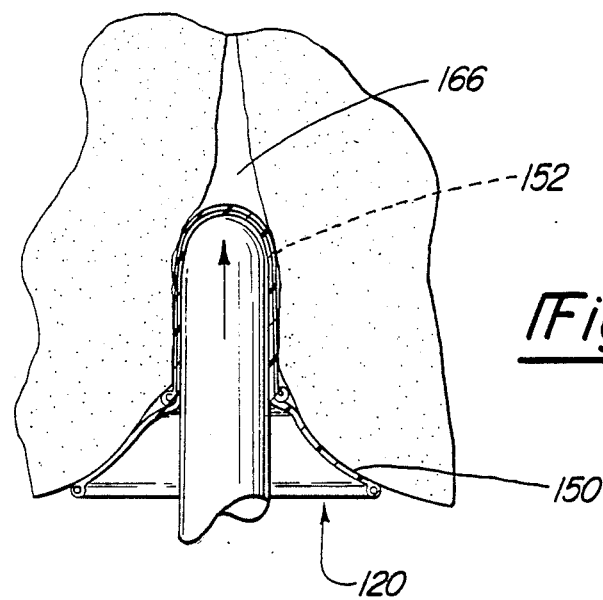
_Fig-15a_
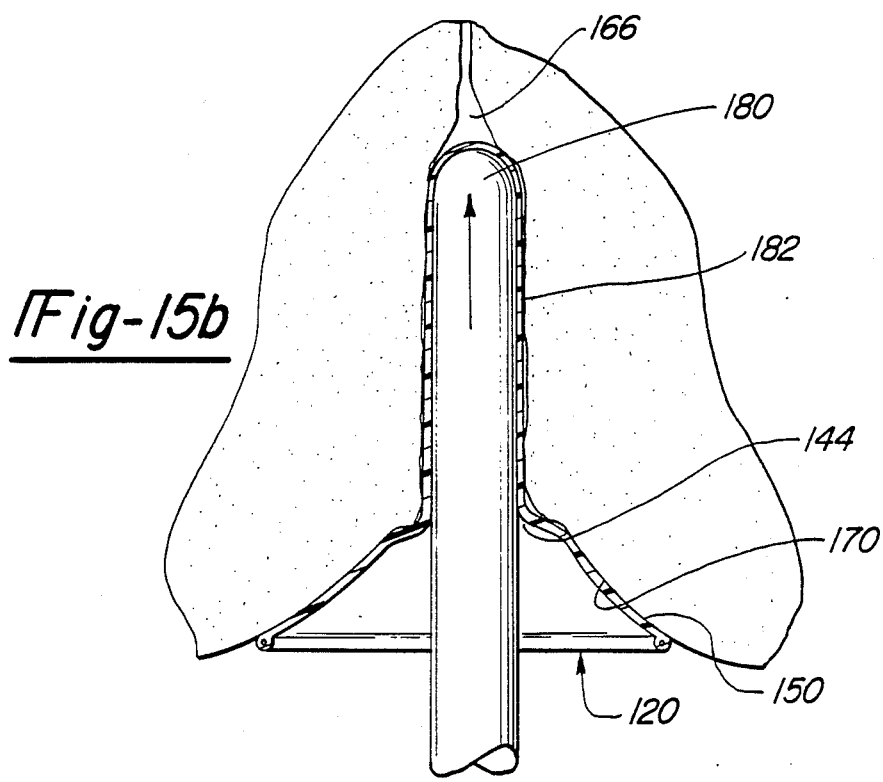
_Fig-15b_

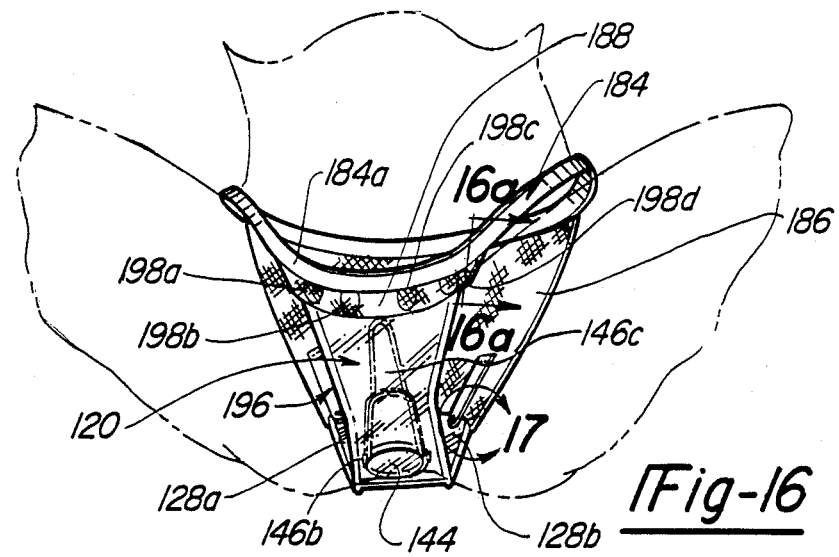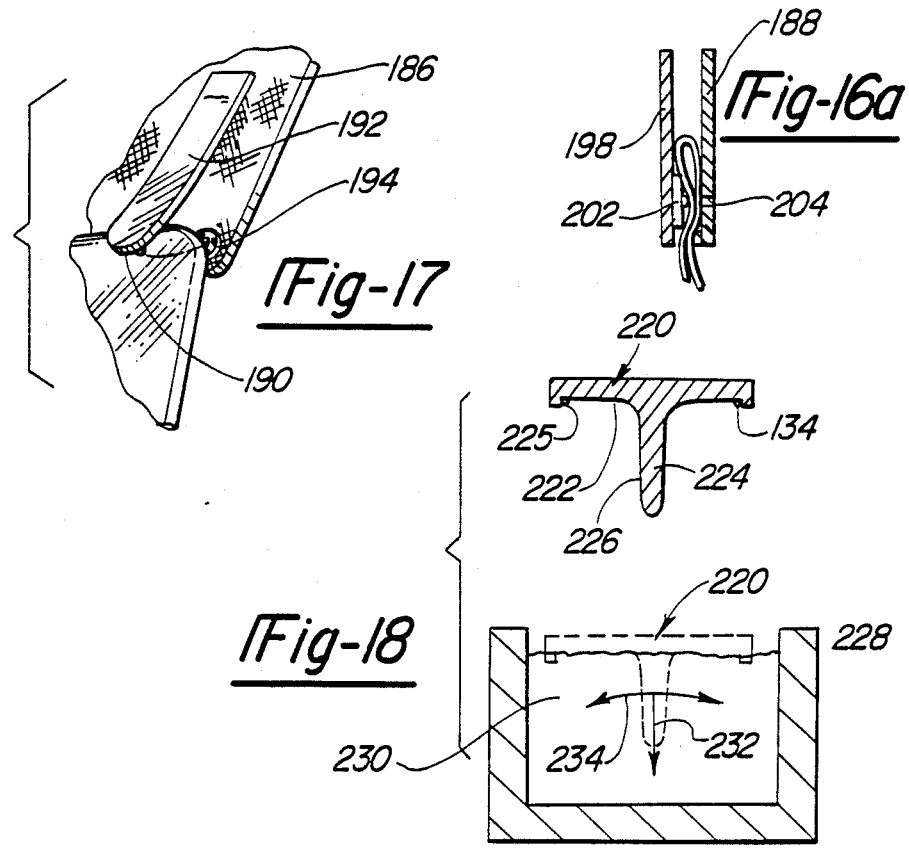

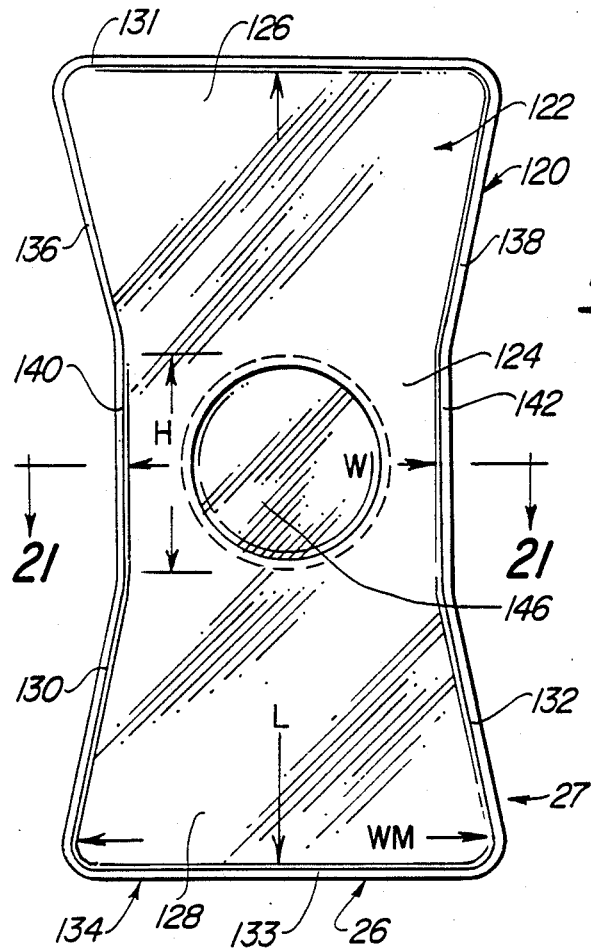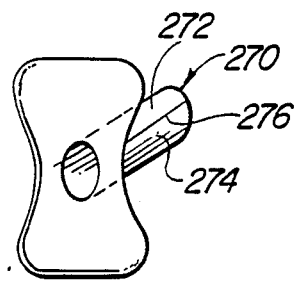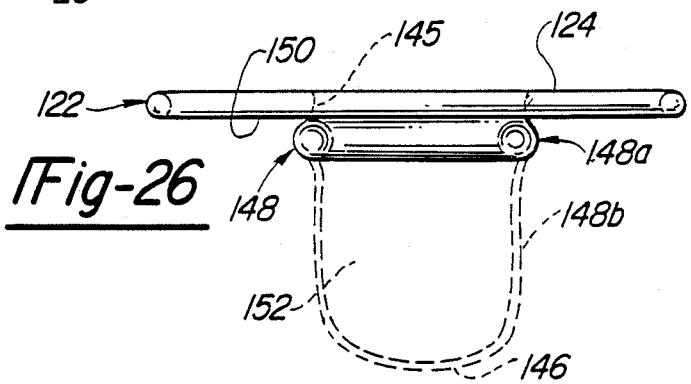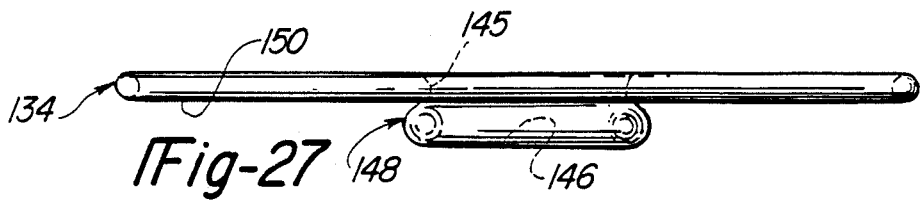

PROPHYLACTIC DEVICE

CROSS-REFERENCE TO RELATED APPLICATION

This application is a continuation-in-part of my copending application Ser. No. 084,622, filed Aug. 11, 1987, now abandoned which, in turn, is a continuation-in-part of my copending application Ser. No. 7,104, filed Jan. 27, 1987, now abandoned.

FIELD OF THE INVENTION

This invention relates to prophylactic devices. More particularly, this invention relates to prophylactic devices which are highly effective in preventing the transmission of venereal diseases and AIDS. Even more particularly, this invention relates to prophylactic devices which may be used by females. The invention even more specifically relates to prophylactic devices of universal application for shielding the perineum of females and males by use of a disposable shield component which is comfortably configured for use in either application.

BACKGROUND OF THE INVENTION

With the widespread occurrence of venereal diseases and AIDS (Acquired Immune Deficiency Syndrome), there is an increasing need for an effective means of preventing the transmission of such diseases through sexual contact. Conventional means for preventing the transmission of such diseases include the use of condoms, diaphragms, gels, creams, etc. However, such conventional means are not totally effective, even when they are used in combination with one another.

There has not heretofore been provided an effective prophylactic device for females persons which prevents the transmission of diseases during sexual intercourse.

The prior prophylactic devices for female persons which have been used heretofore include U.S. Pat. No. 3,536,066 having a bellows proboscis thereon which is joined to a pant style unitized garment without any straps, tapes or buttons thereon. The contraceptive device of the -066 patent includes an insertable portion of a bellows which is positioned in the vaginal canal of a female prior to use. Thereafter, the bellows is expanded by an erected penis to provide for expansion of the bellows during coitus with the female person on which the contraceptive device is used. The device requires preinsertion and does not include means for piloting a large pouch-like member into the vaginal canal. Furthermore, the garment portions thereof are in contact with a large part of the waist region of a user so as to cause possible irritation and discomfort.

U.S. Pat. No. Des. 254,808 to Meldahl discloses a design of a male contraceptive. While the contraceptive appears to be larger in diameter than the average condom, it does not have any structure at the open end thereof to serve as a shield to cover perineum regions of the user of the device so as to prevent passage of bodily fluids to such regions.

German Patentschrifft No. 210413 (1909) discloses a female contraceptive device having a proboscis, or pouch, on one end thereof and having a generally circular collar on the other end thereof which covers a small part of the entrance to a vaginal canal or other bodily orifice.

U.S Pat. No. 4,735,621 likewise shows a thin walled condom-like tubular protective device for insertion in a vaginal canal. It includes a resilient ring on one end thereof to provide an internal anchor, much like a diaphragm.

The prophylactic device of the -621 patent includes a collar on its entrance end which, again, is limited to covering a small part of the entrance to the vaginal canal. The device requires hand insertion to set the internal anchor and thereby exposes a user to bodily fluids and possible transmission of diseases through lesions or the like during the hand transfer and placement of the contraceptive device in the body orifice.

Each of the aforesaid prophylactic devices are characterized by either providing a limited exterior cover at the opening of a body cavity such as a vaginal canal or an anal canal or alternatively a garment type prophylactic device that will cover the full body of a user below the waist. The first type of prophylactic device requires separate hand insertion into the vaginal canal, thereby exposing a user to the bodily fluids therein and the second type of device is uncomfortable if worn for extended periods prior to use.

SUMMARY OF THE PRESENT INVENTION

In accordance with the present invention there is provided a prophylactic device which is adapted to be worn by a person to prevent the transmission of disease and also sperm during sexual intercourse. The device comprises:

(a) An elongated hollow pouch having first and second ends; wherein the first end is closed and the second end includes an opening; wherein the pouch includes a thin wall member which is flexible and preferably elastic;

(b) a continuous flange member which is attached to the second end of the pouch and which extends around the circumference of the opening; and (c) attachment means which is adapted to attach the device to the person.

The prophylactic device of the invention, in one embodiment, can be worn by a female person. In such embodiment the first end of the pouch optionally includes a resilient portion which is adapted to be gripped and retained in position by the muscles in the vagina of the female. In another embodiment the prophylactic device can be worn by a male person. In another embodiment, the prophylactic device is made from two layers of generally inelastic plastic film material joined at the periphery by heat sealing or dielectric bonding.

In yet another embodiment, the prophylactic device is anatomically configured to serve as a universal prophylactic device for either male or female use. The universal prophylactic device has a generally rectangularly configured shield portion that will cover the perineum and the gluteal regions of a male person from the gluteal region of such male person to the scrotum regions of such male person. Such device is dimensioned to cover the perineum region of a female person from the upper pubic region to the perineum region in the vicinity of the anal canal of the female person. Such shield portion prevents the contact of bodily fluids with such perineum regions during use of the prophylactic device. The universal prophylactic device further is characterized as having a rolled pouch segment thereon initially disposed substantially in the same plane as the rectangular shield portion of the prophylactic device. The rolled pouch has a first telescopingly extended piloting position for entry into a body orifice such as a flaccid anal canal of a male person or a vaginal canal of a female person. The pouch is dimensioned to have the smallest dimension thereof greater than the outer dimensions of an erected penis of a male person.

The pouch portion can be extensible inwardly of a body orifice beyond the initial piloting position of the pouch by unrolling and detelescoping the pouch portion into the body cavity during penetration of the erected penis therein so as to define an extended pouch configuration that will permit free lateral movement of a penis within a body orifice.

The pouch can be configured to be fully inserted into a vagina by an erected penis to define a space within the vagina bounded by the pouch and permitting stroking motion of the penis with respect to the clitoral region of the vagina by a rolling motion of a wall segment of the extended pouch therein.

A feature of one embodiment of the present invention is an anatomically configured hermaphroditic prophylactic device which is configured to be fastened on either a female person or a male person to locate a pouch portion thereof for disposition into a body cavity without requiring insertion of a hand or tool into the bodily orifice; and wherein the pouch is connected to a generally rectangularly configured shield that has a width and a length to cover the full perineum of either the female user or the male user when the pouch is disposed in either a vaginal canal or an anal canal during use.

A further feature of the present invention is to provide an anatomically configured hermaphroditic prophylactic device of the type set forth in the preceding object wherein the pouch is preformed to have telescoped segments thereon rolled to form a flat planar prophylactic device which can fit in a preuse position over the perineum of a female or a male user and wherein the telescoped segments are extendable during a first penetration of a male organ into a body cavity to extend a first segment of the pouch portion in a piloted relationship into a first depth of the body cavity and wherein the pouch will unroll into a fully extended further depth position within the body cavity upon continued insertion of the male organ therein.

Yet another object of the present invention is to provide a prophylactic device having the features set forth above wherein the pouch has a minimum interior dimension thereof substantially greater than that of the outer surface dimensions of an erected penis to provide for freedom of movement internally of a bodily orifice such as the vaginal canal of a female user to reduce surface pressure on the penis during coitus by the female user and wherein the length of the pouch is selected to permit an extension and rolling movement of a wall segment portion of the pouch with respect to a clitoral region at the entrance of the vaginal canal to enhance direct pleasurable contact with the clitoral region during coitus.

Still another feature of the present invention is that the prophylactic device having the features set forth above is formed by a dipping process wherein the pouch is formed on a first portion of a mold and the external shield is formed on a second portion of the mold by a relative movement of the mold within a dipping bath of latex or other suitable material for manufacture of a flexible prophylactic device of polymeric material.

Yet another feature of the present invention is to provide an anatomically configured hermaphroditic prophylactic device of the type set forth above and including the method of manufacture as set forth above wherein the prophylactic device can be removed from the mold by first disposing the shield portion in spaced relationship to the mold surface to form telescoped segments on the shield portion and thereafter providing means to roll the telescoped segments into a tight configuration substantially located in the plane of the shield portion previously stripped from the mold and wherein the planar shield and rolled pouch portions are turned end for end to reduce the outer dimensions of the prophylactic device for automatic packaging.

Still another object of the present invention is to provide a packaging process of the type set forth in the preceding paragraph wherein the folding step includes a first end to end folding of the planar disposed shield and rolled pouch portions with a subsequent rolling of the folding segments into a tubular configuration for insertion in a tubular container.

Still another object of the present invention is to provide a packaging process wherein the planar shield and rolled pouch portions are folded end to end three times to form an eight layered compact prophylactic configuration for packaging in flat container configurations.

With the device of this invention, the transmission of diseases and sperm is effectively prevented during sexual contact. The device can be made as a disposable item or as a reusable item. It can be made from inexpensive materials.

The prophylactic device may be in the form of a garment which is worn around the pelvic region. Alternatively, the prophylactic device may be attached to the wearer by other means (e.g., by means of straps, adhesive, tape, etc.).

In yet another embodiment of the invention, the prophylactic device is an anatomically configured hermaphroditic prophylactic device adapted to be connected to a strap configuration which for a male person includes frontal strap segments that will position the anatomically configured shield portion of the hermaphroditic prophylactic device in a clearance relationship with the scrotum of a male person and which further includes short strap segments for extending the shield portion of such a prophylactic device into a full perineum covering relationship with the male person in surrounding relationship to the extendable rolled pouch portion thereof so as to prevent contact of bodily fluids of another person with the perineum region and bodily orifices of a male person user of the prophylactic device. Alternatively, the anatomically configured, hermaphroditic prophylactic device of the present invention may be incorporated as part of a strap support or a bikini pant configuration for a female user. The pant is of a suitable comfortable fabric including an elastic waist portion and an extended buttocks engaging rear portion (or long strap segments) that will position one end of the shield portion of such prophylactic device to cover the perineum of a female person from the anal region thereof to the vulva. The bikini garment or female strap support further includes a frontal portion thereof with short strap segments that connect the opposite end of the shield portion of the such prophylactic device to the waist portion so as to locate the shield portion of such prophylactic device to cover the perineum of a female person from the vulva to the upper pubic region.

In another aspect of the present invention, the strap and/or garment support for locating the anatomically configured, hermaphroditic prophylactic device is connected to the strap or garment components by releasable snap means that are configured to permit noncontact removal of the prophylactic device from the strap or garment components once the prophylactic device has been removed from the user so as to extract the pouch portion of the prophylactic device from the bodily orifice. Consequently, the garment mounted anatomically configured hermaphroditic prophylactic device of the invention can be handled without exchange of bodily fluids to hand or other lesions through which disease can be transmitted.

Still another feature of the anatomically configured hermaphroditic prophylactic device of the present invention is that it is easily removed from standard molding equipment to form a flat form having the perimeter thereof bounded by the planar extent of the shield portion of such prophylactic device and the rolled pouch portion thereof disposed in the same plane as that of the shield and wherein such planar configuration can be first folded on itself and then rolled to form a compact, easily packaged prophylactic component and protecting the pouch at the same time and/or can be folded twice on itself to form a compact, eight layered, generally rectangularly configured unit that is suitable for packaging in flat container packages of various forms and shapes.

Other advantages of the devices of this invention will be apparent from the following detailed description.

BRIEF DESCRIPTION OF THE DRAWINGS

The invention is described in more detail hereinafter with reference to the accompanying drawings, wherein like reference characters refer to the same parts throughout the several views and in which:

FIG. 15a is a view showing the prophylactic device of FIG. 15 in a first extended position for piloting the pouch portion thereof into a body cavity of either a male or a female person;

FIG. 15b is a sectional view showing the pouch portion of the prophylactic device of either FIG. 14 or FIG. 16 in a fully extended position within the body cavity of a male or female person;

FIG. 16 is a diagrammatic view of a further embodiment of an anatomically configured hermaphroditic prophylactic device on a female person;

FIG. 17 is an enlarged fragmentary detail of a releasable fastener for securing a shield portion of the prophylactic devices of either FIG. 14 or FIG. 16 to garments or components thereof;

FIG. 18 is a diagrammatic view of dipping and tilting steps in a process of the present invention for manufacturing anatomically configured prophylactic devices;

FIG. 25 is a front elevational view of another embodiment of the prophylactic device;

FIG. 26 is an end elevational view of the embodiment of FIG. 25;

FIG. 27 is a side elevational view of the FIG. 25 embodiment; and

FIG. 28 is a perspective view of an inelastic plastic film embodiment of the present invention.

DETAILED DESCRIPTION OF THE INVENTION

Figure 1:
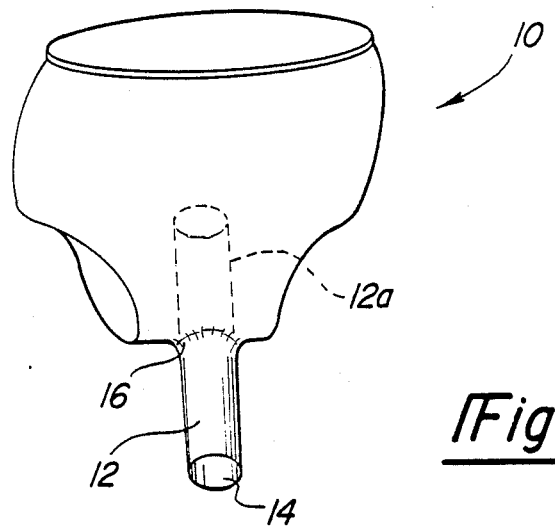
FIG. 1 is a front perspective view of one embodiment of prophylactic device of this invention.
Figure 2:
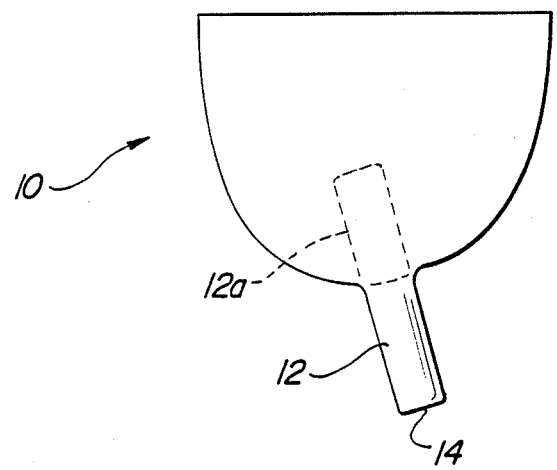
FIG. 2 is a side elevational view of the embodiment of prophylactic device shown in FIG. 1.

In FIGS. 1 and 2 there is illustrated one embodiment of a prophylactic device 10 which is in the form of a garment (i.e., a brief) which can be worn around the pelvic region. The garment includes an elongated hollow pouch 12 having a first end 14 which is closed and a second end 16 which is open.

The pouch has a thin wall member which is flexible and elastic. Preferably the pouch is made of rubber which may be natural or synthetic. Other synthetic materials can also be used (e.g., polyurethane, polyvinylchloride, silicone elastomer, etc.). The thickness of the wall member is in the range of about 0.0005 to 0.1 inch, and preferably in the range of about 0.001 to 0.005 inch.

The second end of the pouch, i.e., the open end is attached to the garment in the manner shown in FIG. 1 is a manner such that a portion of the garment forms a flange around the circumference of the opening in the pouch. Preferably the pouch is molded as an integral part of the garment. Alternatively, the pouch may be formed separately and then bonded to a corresponding opening in the garment. For example, the pouch may be permanently bonded to the garment or it may be detachably connected by means of adhesive, or with snaps, or with a fastener system of the type including an elongated bead or ridge on one component and an expandable receptive groove on the other component (e.g., such as is common with certain sandwich bags).

Figure 3:
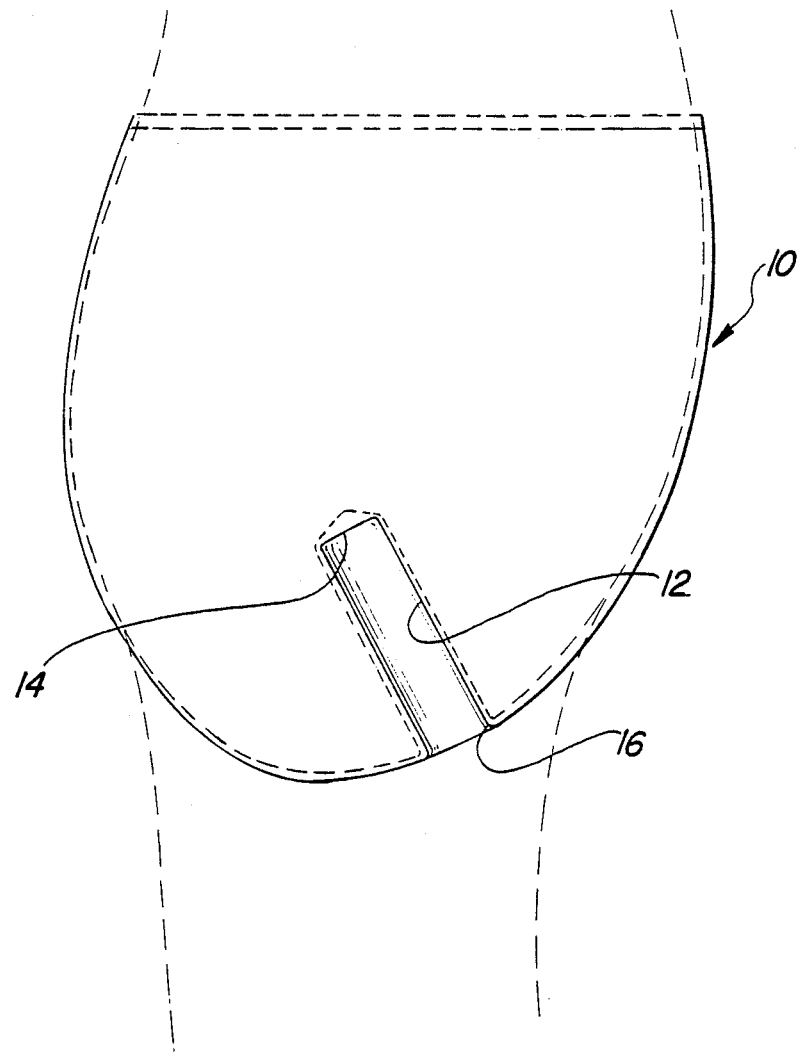
FIG. 3 illustrates the embodiment of prophylactic device of FIG. 1 while being worn by a female person.

As illustrated in FIGS. 1 and 2, the hollow pouch may be invertable. In these views the pouch is shown in dotted lines to illustrate the position of the pouch within the vagina of a female person wearing the garment. When putting on the garment, the pouch may be in the outward position illustrated in these figures. It is also easier to apply desired lubricants and a spermatocide (e.g., such as that commercially available under the name Nonoxonal 9) to either the interior or exterior of the pouch. Typically these materials are applied to both the interior and exterior surfaces of the pouch. Then the pouch is inverted and inserted into the vagina (as illustrated in FIG. 3).

The closed end 14 of the pouch optionally includes a resilient member which is adapted to be gripped and retained in position by the vaginal muscles (i.e., the labia muscles). Thus, when the pouch in inserted into the vagina as illustrated in FIG. 3, the labia muscles are capable of gripping and retaining the end 14 of the pouch in the position shown.

Figure 7:
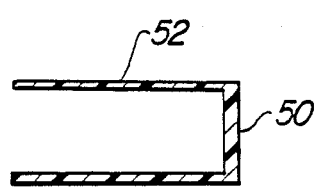
FIG. 7 is a cross-sectional view of a portion of another device of the invention.

The resilient member at the closed end of the pouch may be a resilient disc 50 (as illustrated in FIG. 7) which is preferably flexible. The disc may be made of rubber of plastic. Preferably it is molded as an integral part of the pouch wall 52.

Figure 6:
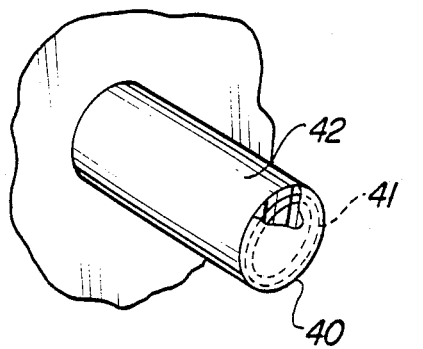
FIG. 6 is a partially cut away, perspective view of another embodiment of prophylactic device of the invention.
Figure 6A:
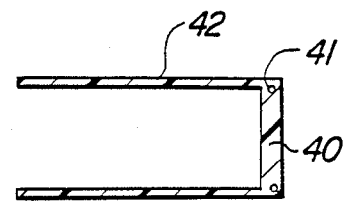
FIG. 6A is a cross-sectional view of a portion of the device of FIG. 6.

Another embodiment of resilient member is illustrated in FIGS. 6 and 6A where it comprises a disc member 40 which includes a ring shaped spring or wire 41. The disc 40 may be deformed or folded to facilitate insertion into the vagina, and then the spring or wire 41 urges the disc member back to its original circular shape. The disc member 40 may be formed as an integral part of the wall member of the pouch 42 or it may be formed separately and then bonded to the wall member.

Figure 4:
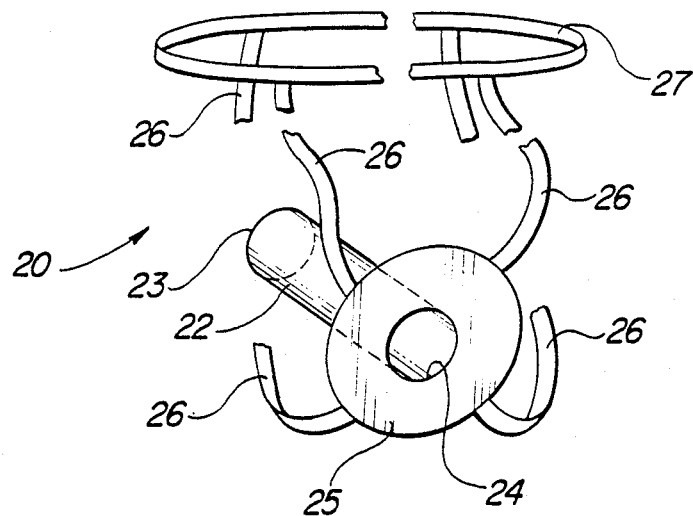
FIG. 4 is a perspective view of another embodiment of prophylactic device of the invention for use by a female person.

Another embodiment of the prophylactic device 20 is illustrated in FIG. 4. In this embodiment, the hollow pouch 22 has a closed end 23 and an open end 24. The open end of the pouch is attached to and surrounded by the continuous flange member 25, as illustrated. The flange extends outwardly at least one inch, and preferably at least three inches, around the open end of the pouch.

The flange member in the devices of this invention may be both flexible and elastic, although neither or such features is required. For example, the flange may be flexible but nonelastic. It is also possible for the flange to be nonflexible (e.g. a plastic member). It is necessary for the flange to be liquid impermeable, however.

In the embodiment shown in FIG. 4, the flange member has a plurality of strap members 26 secured thereto. These strap members are connected at their opposite ends to band 26 which may be worn around the waist or around the pelvic region of the female person using this device. The flange member and the pouch prevent transmission of sperm and diseases from one person to the other.

Figure 5:
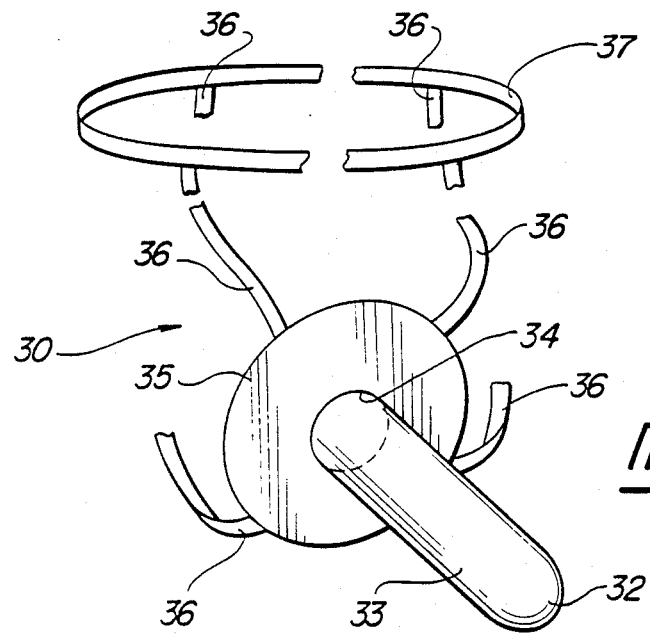
FIG. 5 is a perspective view of another embodiment of prophylactic device of the invention for use by either a male or a female person.

In FIG. 5, there is illustrated another embodiment 30 of prophylactic device of the invention. This embodiment is adapted for use by either a male or female person. The device comprises an elongated hollow pouch or sheath 33 which is closed at its outer end 32. The opposite end 34 is open and it is attached or secured to flange member 35. The flange member extends outwardly around the circumference of the opening in the pouch at least one inch, and preferably at least three inches. Strap members 36 are secured at one end to flange member 35 and are secured at the opposite end to band 37 which may be worn around the waist or around the pelvic region of the person using this device. The pouch and the flange member prevent the transmission of diseases from one person to the other. The pouch also prevents sperm from being transmitted. Of course, the device of FIG. 5 could instead be in the form of a brief to be worn by the person using it, if desired.

Figure 8:
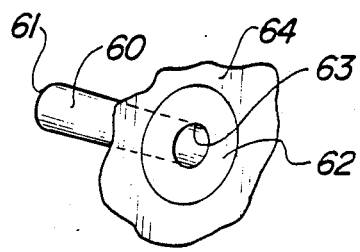
FIG. 8 is a perspective view illustrating another embodiment of prophylactic device of this invention.
Figure 9:
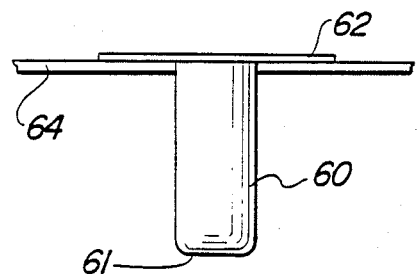
FIG. 9 is a side view of the device illustrated in FIG. 8.

In FIGS. 8 and 9 there is illustrated another embodiment of prophylactic device of the invention in which the pouch member is detachable. Thus, there is shown an elongated pouch member 60 having a closed end 61 and an open end 63. Surrounding open end 63 is a rim member 62 which is adapted to lay against flange 64 and may be detachably secured to flange 64 by means of adhesive, for example. Other useful means for securing rim 62 to flange 64 include snaps, buttons, adhesive tape, bead and groove fastener systems, hook and loop fastener systems, etc. In the arrangement of FIGS. 8 and 9, for example, the pouch member may be detached and discarded after use.

The flange member 64 may be part of a garment (such as illustrated in FIGS. 1 and 2) or it may be the type shown in FIGS. 4 and 5.

Figure 10:
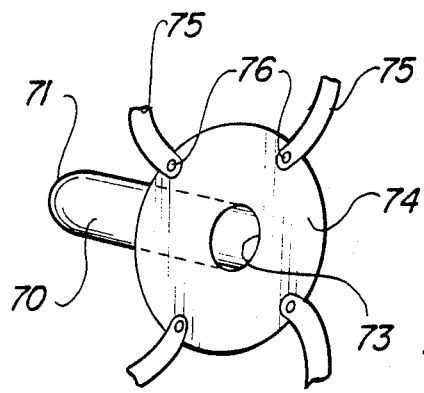
FIG. 10 is a perspective view of another embodiment of prophylactic device of this invention.

FIG. 10 illustrates another embodiment of prophylactic device of this invention. In this embodiment, an elongated hollow pouch 70 has one closed end 71 and an open end 73. Flange member 74 surrounds the circumference of the open end 73, as illustrated. Strap members 74 are detachably secured to flange member by means of conventional snaps 76. Thus the pouch and flange may be detached and discarded after use.

In yet another variation, the pouch member 70 may be used without strap members. For example, the flange 74 may be secured to the skin of the person wearing the device by means of adhesive or with adhesive tape, if desired.

Figure 11:
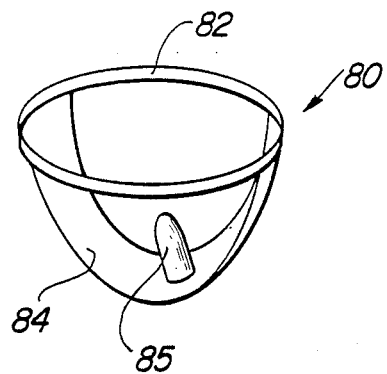
FIG. 11 is a perspective view of yet another embodiment of a device of this invention.

FIG. 11 illustrates another embodiment of device 80 of the invention comprising strap or belt member 82, flange member 84, and elongated hollow pouch 85. The lower end of the pouch is open and the upper end is closed. The flange member extends from one side of the belt to the other, as illustrated.

In the various embodiments of prophylactic devices of this invention, the sizes and thicknesses of the materials may vary. For example, the pouch member may have a length in the range of about 1 to 10 inches (preferably about 4 to 6 inches) and a diameter of about 1 to 4 inches. Although the pouch member may have a uniform diameter throughout its length, the diameter could vary if desired.

The thickness of the wall material of the pouch member and the flange member may also vary. For example, it may be as thin as 0.0005 inch or as thick as 0.1 inch. Preferably it is in the range of about 0.001 to 0.005 inch. The pouch and the flange are preferably made of elastic, impermeable material such as natural rubber or synthetic rubber (e.g., silicone rubber). Useful materials also include nonelastic materials such as plastic (e.g., polyurethane, polyvinylchloride, etc.).

The flange member extends outwardly around the open end of the pouch at least one inch, preferably three inches, and more preferably at least five inches. If desired, the flange member may be thicker than the wall portion of the pouch.

The closed end portion of the prophylactic devices intended for use by female persons may be resilient as described above, although this is not required in each embodiment. It has been found that the pouch is held in position in the vagina by natural physiological force during and after intercourse. The thickness of the closed end portion may vary.

Figure 12:
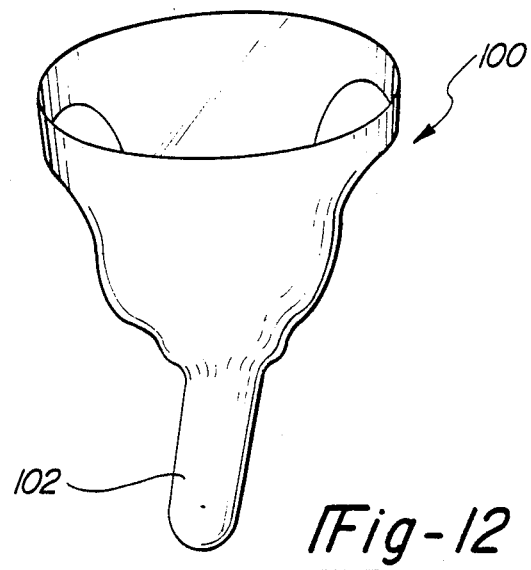
FIG. 12 is a front perspective view of a mold which is useful in the production of a device of this invention.

FIG. 12 is a perspective view of a preferred type of mold 100 which is useful in making devices of the invention which are in the form of a brief. The mold includes a general shape of a brief with an elongated protrusion 102 in the shape and size desired for the pouch member. The mold may be made of any suitable material such as ceramic, glass, hard plastic, etc. The mold is dipped into the material to be used in making the device (e.g., natural rubber latex) and then removed. After the rubber cures or dries, the brief which is so formed can be removed from the mold. Leg openings are made in the sides of the brief.

Figure 13A:
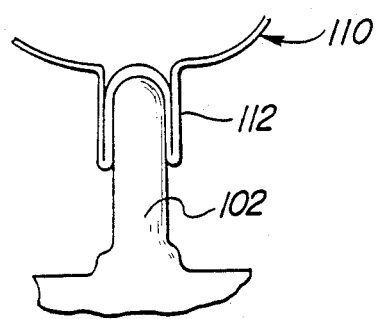
FIGS. 13a and 13b illustrate a preferred manner of telescoping and rolling the pouch member of a device of this invention.
Figure 13B:
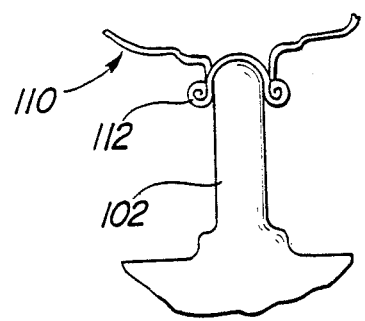

FIGS. 13a and 13b illustrate a preferred and convenient manner for telescoping and rolling the pouch member during manufacture and packaging (i.e., prior to sale). As illustrated, the pouch member 112 of the device 110 is partially inverted as the device is being removed from the protrusion portion 102 of the mold. When the pouch is approximately one-half inverted, it has the appearance shown in FIG. 13a. Then the pouch member is rolled upon itself toward the flange member, as illustrated in FIG. 13B until it is completely removed from the protrusion 102 of the mold. For example, brushes may be used to roll the pouch in this manner.

Figure 13C:
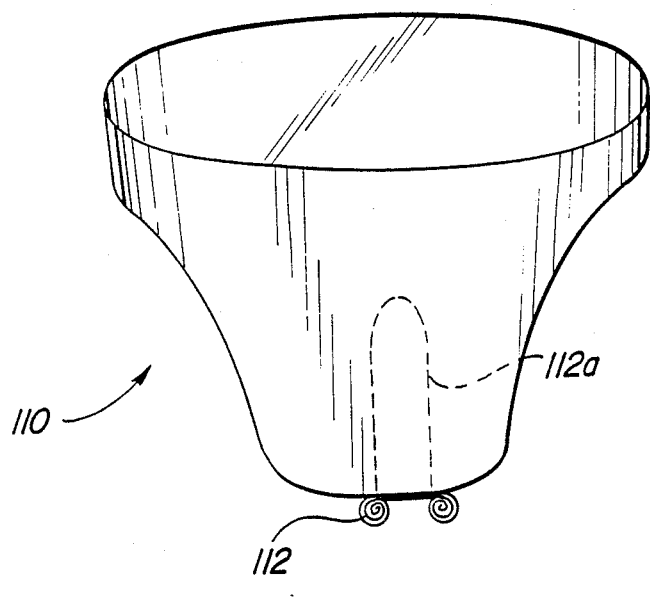
FIG. 13c shows a device of the invention in which the pouch member is rolled.

FIG. 13c illustrates the entire brief with the pouch member completely rolled. The brief may be worn in this form until the time of intercourse; then the pouch will easily unroll and extend into the vagina to the position illustrated by dotted line 112A.

Another embodiment of the present invention is illustrated in FIGS. 25 through 27. They show an anatomically configured, hermaphroditic prophylactic device 120. The folded unit 120 includes a generally rectangularly configured shield portion 122 having a narrow central segment 124 and a pair of end wing segments 126, 128. The wing segments 126, 128 have a gradually tapering width which is bounded by a pair of segments 130, 132 of a continuously formed peripheral bead 134 which converge from a first end segment 133. A like pair of bead segments 136, 138 formed on the sides of the wing portion 126 converge from a second end segment 135 of the peripheral bead 134. Segments 136, 138 are joined to central bead segments 140, 142 that are located in spaced parallelism. They are joined respectively to the inwardly convergent bead segments 130, 132.

The prophylactic device 120 further includes an integrally formed pouch 144 that is centered in the center region 124 of the shield portion 122. The pouch 54 has an entrance opening 145. The pouch portion includes an end closure 146 that is joined to a rolled ring 148 that is formed during a manufacturing process to be described. The rolled ring 148 and the end closure 146 are located on the inner surface 150 of the prophylactic device 120. More particularly, the inner surface 150 has a length from the extreme ends of the wing portions 126, 128 and a width at the center region 124 to anatomically fit either a male or female user to provide complete coverage of the perineum regions of a user to prevent bodily fluids from contacting such regions during use of the prophylactic device 120. As shown in FIG. 26, the rolled ring 148 has a prepackaged position 148a, a piloting position 148b and a fully extended position 148c (FIG. 15d).

More specifically, in the illustrated arrangement, the shield portion 122 has a length L in the order of 22 cm. The maximum width WM of the wing portions 126, 128 is in the order of 12 cm and the center region 124 has a width W of 9.5 cm and a height H of 6 cm. The wall thicknesses of the shield portion 122 and of the pouch 144 can be selected from the ranges discussed with respect to the embodiment of FIGS. 1 and 2 and the other various embodiments.

The aforesaid dimensions are configured to anatomically relate to the perineum region of either a female user of the device or a male user of the device wherein the pouch 144 can be rolled from its stored position in close spaced parallelism with the plane of the shield 122 to an extended position within a body cavity of a user.

One aspect of the present invention is that the rolled ring portion 148 is configured so that the pouch 144 will unroll to form a single wall piloting segment 152 shown in dotted line configuration in FIG. 26 upon first entry into the body cavity. The piloting segment 152 will be carried by further entry into a body cavity by unrolling the rolled ring segment 148 from the shield portion 122 until the pouch 144 is fully disposed as depicted at 155 within the body cavity (FIG. 15d).

Figure 14:
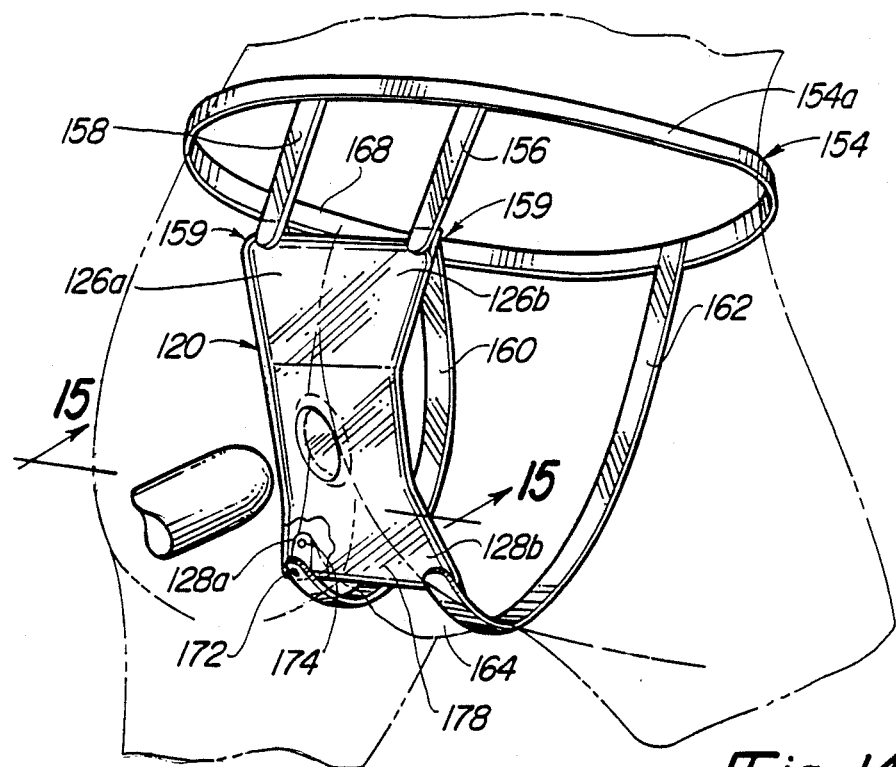
FIG. 14 is a perspective view of an anatomically configured hermaphroditic embodiment of the invention on a male person.

One use representation of the prophylactic device 122 of the embodiments 25 through 27 is somewhat diagrammatically illustrated in FIG. 14. In this representation, the prophylactic device 120 is secured to a strap system 154 that includes an elastic waist segment 154a that is in surrounding relationship to the waist of a male user. The strap system 154 includes a pair of straps 156, 158. Each strap 156, 158 has fastener means 159 secured to corner segments 126a and 126b of the wing portion 126. The strap system 154 further includes a pair of front located long straps 160, 162 that are connected at one end to the waist segment 154a and at the opposite end thereof to corner segments 128a, 128b of the wing portion 128. The arrangement positrons the shield portion 122 to cover the perineum region of a male user from the genital region 164 thereof to a region above the anal canal 166 in the vicinity of the coccyx region 168 of the male user.

Consequently, closure wall 146 of the pouch 144 is positioned in alignment with the anal passageway 166 while the bead portions 140, 142 of the center region 144 are located in bridging engagement with the perineum 170 of the male user to shield such perineum regions from bodily fluids during use of the prophylactic device 120.

Figure 15:
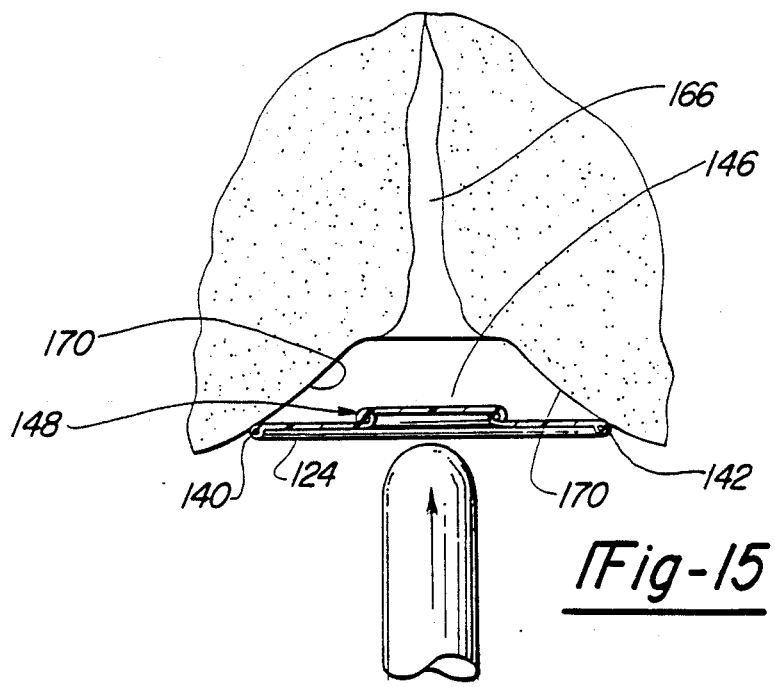
FIG. 15 is a fragmentary sectional view taken along the line 15—15 in FIG. 14.

As shown in FIG. 15, the rolled ring 148 is located out of bodily contact with the user so as to permit comfortable wear of the prophylactic device 120 prior to use. Upon use, the inside and outside of the closure wall 146 can be suitably lubricated. Initial penetration into the body cavity represented by the anal passageway 166 causes the piloting segment 152 to separate from the rolled ring 148 to form a piloted entrance and release of the pouch 144 into the anal canal 166. The pouch 144 is completely unrolled as shown in FIG. 15b upon further penetration of the anal canal 166 so as to dispose the inner surface 150 of the prophylactic device 120 in full shielding relationship with the perineum 170 during use. The full shielding relationship extends side to side of the perineum region 170 and from a region in the vicinity of the scrotum region 164 to the gluteal region.

In accordance with the present invention, the extent of the shielding by the anatomically configured prophylactic device 120 is selected to provide desired full coverage of a perineum region 170 of a male user without contacting extensive portions of the exterior body surface of the user in a manner which could cause discomfort. Nevertheless, the extent of the anatomic dimensions of the shield portion 122 are able to cover the aforedescribed perineum region 170 to prevent the exchange of bodily fluids between the user of the prophylactic device and a person penetrating and extending the pouch 144 of the device, thereby to provide desired protection during use of the prophylactic device 120.

A further feature of the present invention is that the strap system 154 is readily connected to and disconnected from a prophylactic device 120 prior to and following use so as to enable the prophylactic device 120 to be removed from the anal channel (or other body cavity) following use without an exchange of the bodily fluids to a person handling the pouch. More specifically, in order to assure such separation, the connections at each of the corner portions 122a, 122b, 128a, 128b is by use of a simple snap configuration including a male snap portion 172 that is secured to the end of the strap system 154 and a female snap portion 174 on a split segment 176 of each of the straps as shown on the strap 160 at the corner 128a in FIG. 14.

The arrangement enables the user to remove the strap system 154 and attached prophylactic device 120 from the user. The inside shielded portion of the surface 150 can then be grasped at the split strap segment 174 to unfasten the strap ends from the used prophylactic device 120. The system enables the prophylactic device 120 to be removed following use without unnecessary hand contact with bodily fluids on the outer surface 178 thereof.

Most bodily fluids shielded by the prophylactic device 120 are concentrated within the interior cavity 180 of the extended pouch, which is shown at 182 in FIG. 15b.

The anatomically configured, hermaphroditic condom 120 shown in FIGS. 25 through 27 is equally suitable for use on a female person as shown in FIG. 16. In this embodiment, the prophylactic device 120 is representatively shown as being connected to a bikini-like panty garment having an elastic waist portion 184 with a buttocks engaging back panel 186 and a shallow frontal segment 188. The back garment panel 186 is connected to the corner regions 128a, 128b of the wing segment 128 by male snap segments 190 on straps 192 to engage female snap components 194 secured to the corner of the rear panel 186 of the bikini-like garment. A like snap fastener assembly 196 connects the opposite corner of the rear panel 186 to the corner region 128a of the wing portion 128. The front segment 184a of the elastic waist carries a plurality of straps 198a, b, c, and d each having a male snap formed thereon which, as shown in FIG. 16a includes a male fastener element 202 on the strap 198a which is pressed through the corner segment or an edge of the wing segment 126 to engage a female snap element 204 on the inner surface at the lower edge of the shallow frontal segment 188.

The garment for carrying the prophylactic device 120 can also be in the form of a strap system as shown in FIG. 14 in which case the small straps 156, 158 will be located on the front of a female and the back long straps 160, 162 will extend around the rear buttocks of a female user of the prophylactic device 12. In either case, the prophylactic device 20 is located so that the end closure 146 is disposed in covering relationship to the vulva 204 at the entrance to a vaginal canal 202 (FIG. 15d). The inner surface 150 of the shield portion 122 is thus disposed in protective overlying juxtaposed relationship with the vulva 204 and also covers the perineum regions 208 of the user extending from the upper region of the pubic area to the perineum in the region of the anal orifice or canal of the female user. Thus, a substantial portion of the bodily surface of a female user is covered by the anatomically configured, hermaphroditic prophylactic device 120 without placing a substantial portion of an elastic or plastic like synthetic material against the outer surface of the user. Consequently, the device can be worn prior to use without discomfort.

Figure 15C:
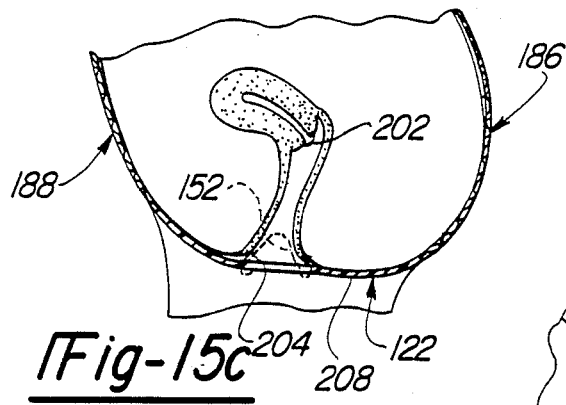
FIG. 15c is a sectional view showing the dimensional relationship of an anatomically configured hermaphroditic prophylactic device with the pouch portion thereof extended and in spaced relationship to an erected penis within a vaginal canal to provide freedom of and lateral movement with respect to the inner walls of the extended pouch portion of such prophylactic device.
Figure 15D:
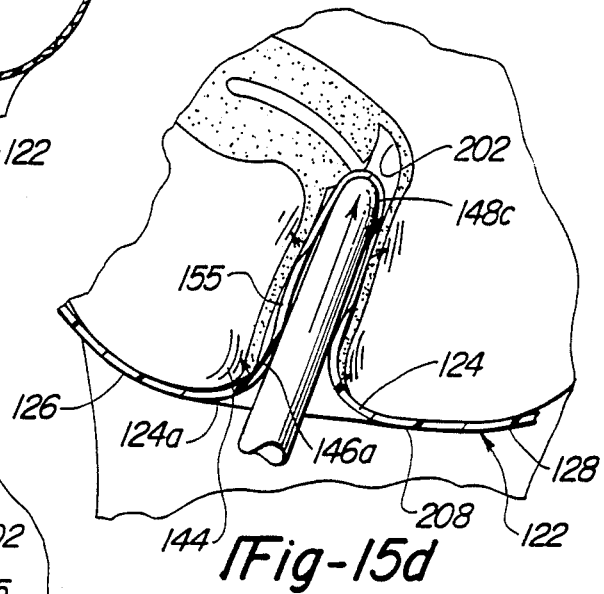
FIG. 15d is a fragmentary view of the pouch wall at the clitoral region of a vaginal canal.
Figure 15E:
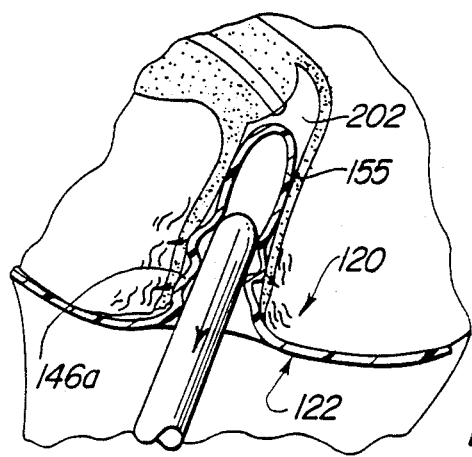
FIG. 15e is a fragmentary view of a stroking roll in the pouch wall of FIG. 15d.

The initial position of the prophylactic device 120 is shown in FIG. 15c at which point a portion of the exterior body surface of the female is covered by the contraceptive device 120 to protect against bodily fluid exchange during normal use. The prophylactic device 120 can be carried either on a strap system of the type shown in FIG. 14 or on a bikini like garment. Prior to extension of the rolled pouch 144 the prophylactic device 120 is disposed in overlying relationship but out of engagement with the vulva 204 and other portions of the female person using the prophylactic device. The end closure 146, however, is positioned for ready disposition of the piloting segment 152 of the pouch 144 into the vaginal cavity 202 when a penis is inserted thereagainst to extend the pouch freely into the vaginal cavity 202. The length of the pouch 144 is greater than that of an erected penis and will have a dimension which is great enough to extend the pouch to form a loose fitting cover of the walls of the vaginal cavity 202 as shown in FIG. 15c in diagrammatic form.

One feature of the present invention is that a forwardly located wall segment 146a of the extended pouch is located in overlying relationship to the clitoral region of a female user. Stroking movement of the penis within the vaginal canal will occur without undue contact between the glans region of the penis and the walls of the extended pouch 155. The wall segment 146a is joined to the flat shield portion 122 at an exterior anchor point 122a thereof. The exterior anchor point 122a and the wall segment 146a are operative during insertion and withdrawal of a penis from the interior of the extensible pouch to produce a rolling of the wall section 146a for pleasurably stimulating the clitoral region during intercourse. Consequently, the prophylactic device 120 will not interfere with pleasurable use thereof during coitus.

Figure 19:
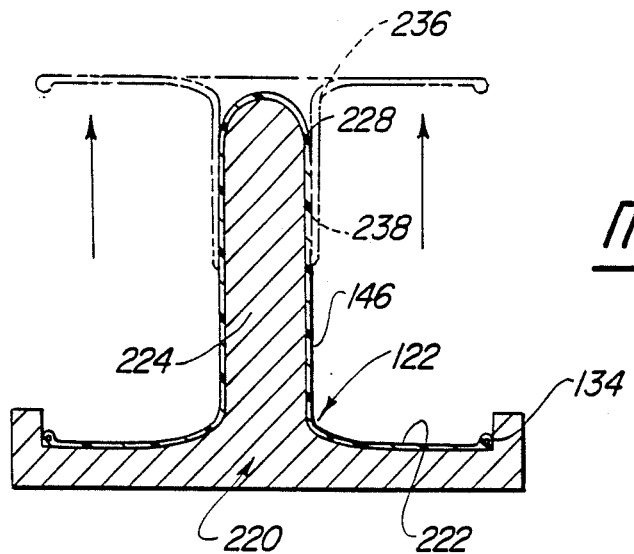
FIG. 19 is a diagrammatic view showing a stripping step of such process steps of FIG. 18.
Figure 21A:
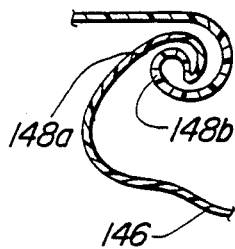
FIG. 21a is an enlarged sectional view of a segment of a partially detelescoped pouch.
Figure 20:
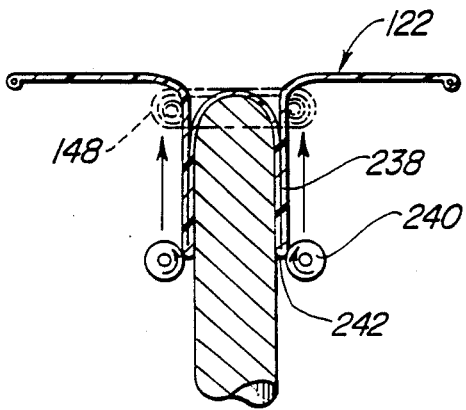
FIG. 20 shows a rolling step wherein telescoped segments of the pouch are rolled into generally the same plane as that of the shield portion of such prophylactic device.
Figure 21:
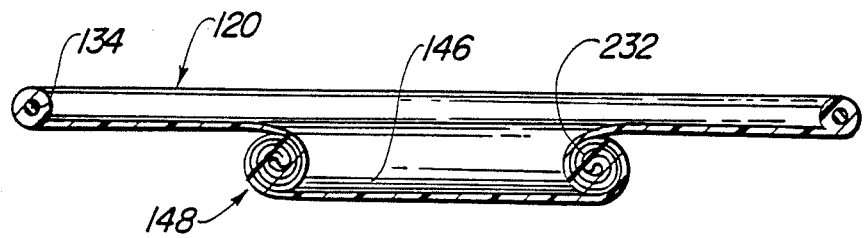
FIG. 21 is a sectional view taken along the line 21—21 of FIG. 25.

In accordance with other aspects of the present invention, the prophylactic device 120 of the present invention is formed by a process as set forth in FIGS. 18 through 20.

The process includes a mold 220 having a flat surface 222 thereon of a planar extent corresponding to that of the planar extent of the shield portion 122 bounded by the bead 134. The bead 134 is initially disposed at a bead support ridge 126 around the periphery of the flat surface 122. The flat surface 222 has a protuberance 224 extending outwardly. The protuberance 224 has an outer surface 226 thereon dimensioned to correspond to that of the inside surface of the extended pouch 155.

In practicing the invention, the mold 220 is connected to suitable carriage means for movement into an open ended container 228 that has a body of synthetic or latex material 230 therein of a composition as discussed in the earlier embodiments, which can be deposited on the surfaces 222, 226 to form a resultant thin layer deposit thereon. The deposit can be formed by a single or double dip process which includes directing the mold 220 along a path 232 into the body of material 230 to form a layer of material on the surface 226. When the mold 220 is located in the dotted line position shown in FIG. 18, it can be tilted about an arc 235 so as to deposit a thin layer of material across the surface 222.

The resultant deposited material is shown in FIG. 19. The deposited material is stripped from the mold 222 by relative movement between the formed shield portion 122 and the flat surface 222 of the mold 220 whereby the shield portion 122 assumes the dotted line position shown by reference numeral 236 in FIG. 19. This causes the pouch portion of the prophylactic device to be telescoped upon itself to form a double wall telescoped segment 238. The double walled telescope segment 238 is then engaged by suitable means such as rollers 240 to roll the telescoped double wall portion 238 upon itself from a return bend portion 242. The resultant rolled ring 148 has an outer wall segment 148d which will unroll as the ring 148 assumes its piloting position 148b. It has an inner wall segment 148e which will unroll after the pilot portion 152 is positioned. This rolled ring 148, as previously discussed, disposes the end closure 146 of the prophylactic device in close spaced parallelism with the bead 134 which has latex formed therearound to form the perimeter of the prophylactic device 120.

Figure 22:
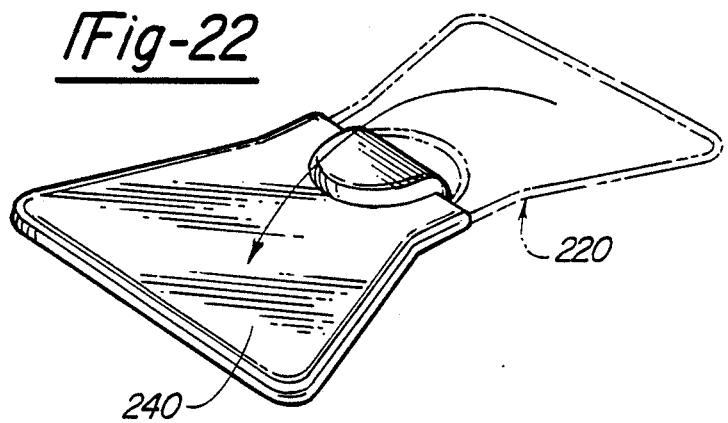
FIG. 22 is a perspective view of a first fold step in packaging a prophylactic device formed by the steps of FIGS. 18 through 20.
Figure 23:
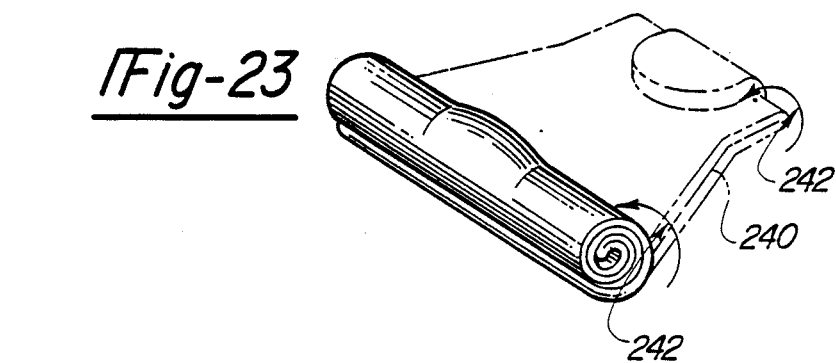
FIG. 23 is a rolling step for configuring the folded prophylactic device of FIG. 22 in a tubular form for subsequent packaging.
Figure 24:
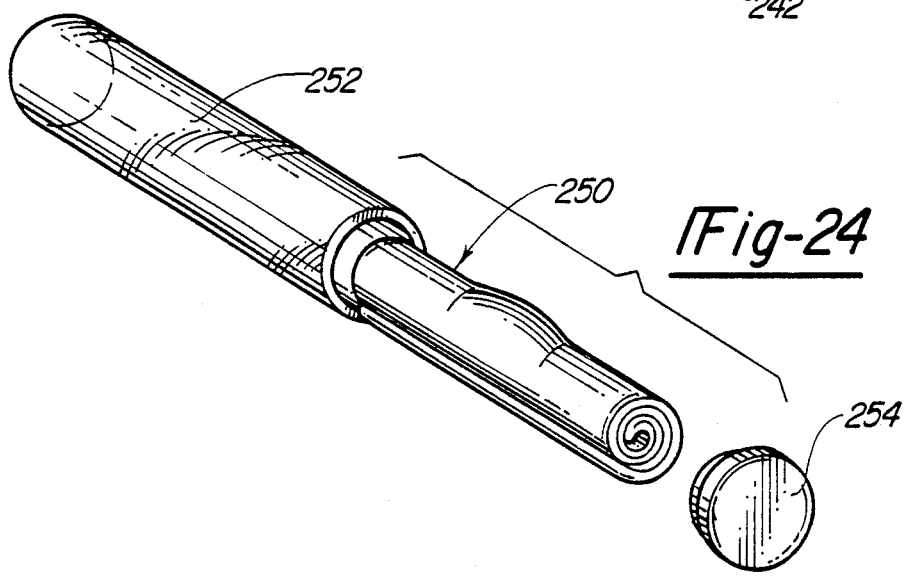
FIG. 24 is an exploded view of a folded and rolled prophylactic device in an aligned, preassembled relationship with a tubular container for such prophylactic device.

The rolling of the ring 148 will remove the prophylactic device 120 from the form 220. The removed prophylactic device 120 can then be readily manipulated for various forms of storage. For example, in FIGS. 22 through 24, the prophylactic device 120 removed from the mold 220 can be folded end to end and then rolled from a joined end portion 240 to form a tubular configuration shown at 250 in FIG. 24. The tubular configuration is readily insertable into the interior of an elongated container 260 which is representatively shown as having a cap closure 262. In this arrangement, each of the individual prophylactic devices 120 are packaged separately from the garment or strap systems for connecting the prophylactic device 120 for male or female use. As previously discussed, the universal prophylactic device is anatomically configured to extend over the perineum regions of either a male or a female user to shield such regions from bodily fluids during use.

Figure 22A:
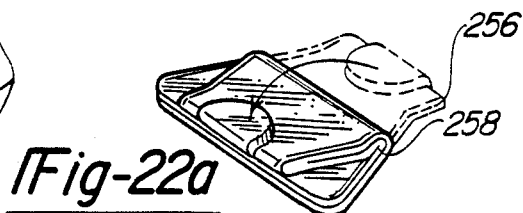
FIGS. 22a–22c are perspective view of an embodiment for folding the prophylactic device.
Figure 22B:
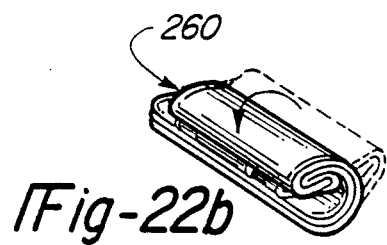
Figure 22C:
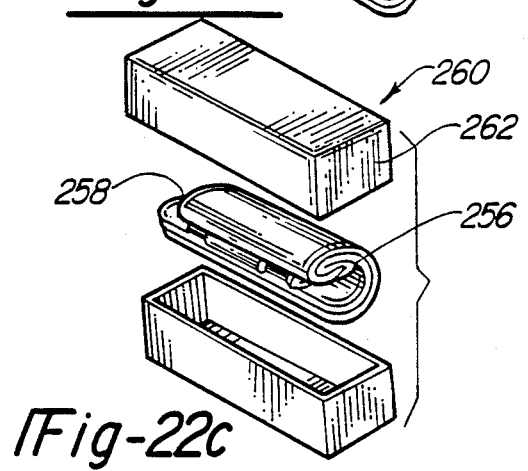

The prophylactic device 120, as stripped from the mold 220, is also readily foldable as shown in FIG. 25 to form a first joined end region 256 which can be folded on itself to form a second folded end region 258 that can be made even more compact by folding back upon itself to form a third fold region 260 thereby to define an eight layered compact condom package 262 that is readily adapted for packaging in compact, flat container configurations representatively shown at 264 in FIG. 22c.

In yet another embodiment of the invention, shown in FIG. 25, a plastic pouch 270 is formed from two thin film sheets 272, 274 of plastic that are joined at their periphery 276. Suitable plastic film material contemplated by the invention includes polyvinylchloride, polyurethane or polypropylene. The pouch 270 in this embodiment can be inelastic. However, it is dimensioned to provide freedom of movement of an erected penis with respect to a shielded vaginal canal and is also configured to be rolled and unrolled with respect to a shield portion 278 of a configuration like shield portion 122. In this embodiment, the pouch 270 has a flange 271 for attachment by suitable means around an entrance opening 280 in the shield portion.

Other variants are possible without departing from the scope of the present invention.

What is claimed is:

1. An anatomically configured prophylactic device adapted to be worn by a female for insertion into a vaginal cavity to prevent the transmission of disease and bodily fluids during sexual intercourse, said device comprising:

a flat shield portion having a central region of a width to span the perineum and having a preselected length bounded by opposite ends spaced apart by a distance to form a spaced shielding of the user at only a portion of the perineum of the user which is susceptible to exposure to bodily fluids during intercourse with the user;

said flat shield portion having a length which will cover only the outer body surfaces of the perineum of a female from the upper pubic region to a point closely adjacent the anal canal;

said flat shield portion having an exterior surface which is free of outwardly directed projections and having an inboard surface engageable with the perineum of the user and said flat shield portion further including means for connecting to strap means for disposing the flat shield portion in overlying relationship with the perineum region;

a pouch being a plain tubular elastic member of uniform wall thickness and with a smooth surface wall located solely between said inboard surface and the perineum of the user, said pouch having an entrance formed integrally with the central region of said flat shield portion and having a diameter greater than that of an erected penis to be inserted into said pouch;

said pouch being formed prior to use as a fully rolled ring always located inboard of said inboard surface adjacent the perineum of a user in overlying relationship to the vagina, said rolled ring surrounding said entrance at said inboard surface of said flat shield portion and including two fully telescoped smooth-walled segments and a return bend joining said telescoped segments deployable to form a pilot portion and a partially unrolled ring segment for maintaining the pilot portion in a piloting position internal of a vagina;

said pouch including an end closure wall located in substantially the plane of said flat shield portion when said pouch is a rolled ring, said end closure wall in alignment with the entrance to the vagina of a user, said end closure wall engageable by an erected penis to deploy said pilot portion by partially unrolling said rolled ring from said inboard surface in the direction of the perineum while directing said pilot portion interiorly of the entrance to the vagina;

said partially unrolled segment of said pouch being disposed against said inboard surface following deployment of said pilot portion for maintaining said pouch in its piloting position for further extension of said pouch interiorly of the vagina;

said pouch having a diameter greater than that of an erected penis and having a length longer than an erected penis when fully extended and being extended from said inboard surface by directing a member through said entrance and against said end closure at a point inboard of said inboard surface to produce a first unrolling of said rolled ring to deploy said pilot portion and to produce a second unrolling of said partially rolled segment of said rolled ring to fully extend the pouch into the vagina to loosely cover the internal walls of the vaginal canal while remaining loosely draped on the outer surface of the penis; and said extensible pouch remaining positioned in its fully deployed position by said means for connecting to strap means while positioning the flat shield portion in a position to cover the perineum region from the upper pubic region to the anal cavity.

* * * * *